United States Patent [19]
Paciorek et al.

[11] Patent Number: 4,788,312
[45] Date of Patent: Nov. 29, 1988

[54] TRISILAHYDROCARBON LUBRICANTS

[75] Inventors: Kazimiera J. L. Paciorek, Corona del Mar; Robert E. Pratt, South Pasadena; Joseph G. Shih, La Palma, all of Calif.

[73] Assignee: Technolube Division Lubricating Specialties Co., Los Angeles, Calif.

[21] Appl. No.: 169,225

[22] Filed: Mar. 16, 1988

[51] Int. Cl.$^4$ ................................................. C07F 7/08
[52] U.S. Cl. .................................... 556/435; 552/465; 252/49.6
[58] Field of Search ............................... 556/435, 465

[56] References Cited
U.S. PATENT DOCUMENTS

| | | | |
|---|---|---|---|
| 2,632,013 | 3/1953 | Wagner et al. | 556/435 X |
| 2,637,738 | 5/1953 | Wagner | 556/435 X |
| 2,721,873 | 10/1955 | MacKenzie et al. | 556/435 X |
| 2,740,802 | 4/1956 | Wagner et al. | 556/435 |
| 3,296,296 | 1/1967 | Webster | 556/435 X |
| 3,347,897 | 10/1967 | Webster | 556/435 |
| 3,580,940 | 5/1971 | Webster | 556/435 |
| 3,595,733 | 7/1971 | Ching et al. | 556/435 X |
| 3,658,865 | 4/1972 | Bakassian et al. | 556/435 X |

Primary Examiner—Paul F. Shaver
Attorney, Agent, or Firm—Thomas A. Schenach

[57] ABSTRACT

Trisilahydrocarbon synthetic lubricant base stocks are prepared by the reaction of dienes containing four to sixteen carbon atoms with dihalosilanes, followed by further reaction of the bis(alkenyl)dihalosilane intermediates with trihalosilanes or trialkylsilanes, followed by substitution of the halogen atoms in the second intermediates by organometallic compounds or by hydridometallic compounds plus olefins.

5 Claims, No Drawings

TRISILAHYDROCARBON LUBRICANTS

RIGHTS OF THE GOVERMENT

This invention was made with Government support under Contract No. F33615-86-C-5099 awarded by the Department of the Air Force. The Government has certain rights in the invention.

BACKGROUND OF THE INVENTION

This invention relates to synthetic lubricant base stocks based on silane chemistry and to chemical intermediates useful in their preparation. More particularly, it relates to a novel family of trisilahydrocarbons prepared from di halo silane, diolefins, trihalo- and trialkylsilanes, and organometallic and hydridometallic compounds through novel alkenylhalosilane intermediates.

Deficiencies in the properties and stability of petroleum base stocks historically used in the formulation of lubricants, hydraulic fluids, and functional fluids have led to the development of a wide variety of synthetic base stocks—for example, polyalphaolefins, esters, silicones, perfluorinated polyethers, and the like. These base stocks which are prepared through specific chemical syntheses rather than by the refining of crude oils, have numerous advantages over conventional petroleum oils. They are particularly useful in aerospace, military, and other specialty applications which involve extremes of temperature, vacuum, hostile chemical environments, and the like, in which conventional petroleum-based products do not hold up.

Among the classes of synthetic lubricant base stock that have shown promise in many of these specialty applications are the alkylsilanes or monosilahydrocarbons, $$CH_3—Si (R'R''R''')$$

wherein R', R", and R''' are alkyl groups having from six to twelve carbon atoms. These monosilahydrocarbons are described, for example, in C. E. Snyder et al., *ASLE Transactions*, vol. 25, No. 3, pp. 298–308 (1982). These monosilahydrocarbons have been shown to be superior to synthetic hydrocarbons such as the polyalphaolefins in viscosity-temperature properties, oxidative stability, and especially thermal stability, while additionally having advantages over silicones (polysiloxanes) in lubricity and bulk modulus. It is evident that incorporation of the silicon atom into the hydrocarbon skeleton can improve the utility of the structure for synthetic lubricant purposes.

However the desirable effects of the silicon atom in the monosilahydrocarbons of the prior art become attenuated as the alkyl chains therein are increased beyond a certain length. Monosilahydrocarbons containing for example ninety or more carbon atoms would almost certainly be solids, not fluids, at room temperature. Moreover obtaining the chemical raw materials (high molecular weight olefins or alkyl halides) in the necessary purity required for the syntheses of high molecular weight monosilahydrocarbons is extremely difficult. Thus, within the class of monosilahydrocarbon synthetic lubricant base stocks, it is the lower molecular weight members which are useful in applications wherein a lower fluid viscosity is required and where some degree of volatility can be tolerated. Liquid space lubricants, however, are frequently required to have extremely high viscosities and extremely low volatilities, and for such applications the monosilahydrocarbons of the prior art, because of their relatively low molecular weights, are not suitable.

It would be highly desirable to have available a class of silahydrocarbons which retain desirable characteristics of the monosilahydrocarbons of the prior art, but which could be prepared in a wider range of molecular weights, viscosities, and volatilities, so as to be suitable not only for the lower-viscosity applications currently satisfied by the prior art materials but for the high-viscosity low-volatility applications as well. It would be further desirable if this new class of silahydrocarbons could be prepared from readily accessible raw materials. It would be additionally desirable to have available relatively simple silicon-containing chemical intermediates, which by the proper choice of reagents could be converted into numerous silahydrocarbon structures designed to have properties suitable for specific applications. Our invention satisfies all of these objects.

PRIOR ART

We are not aware of the use of trisilahydrocarbons of our invention in synthetic lubricant applications. These trisilahydrocarbons and the chemical intermediates employed in their preparation and disclosed herein are, to the best of our knowledge, new chemical compounds previously unknown.

DETAILED DESCRIPTION OF THE INVENTION

We have discovered a novel class of synthetic lubricant base stock consisting of trisilahydrocarbons having the general structure $$R_1R_2—Si[—A—Si(R_3R_4R_5)]_2$$

wherein $R_1$, $R_2$, $R_3$, $R_4$, and $R_5$ represent alkyl groups having from one to twelve carbon atoms and —A— represents an alkylene group having from four to sixteen carbon atoms. It is preferable that the alkyl and alkylene groups be unbranched—that is, —A— is preferably —$(CH_2)_n$— wherein n is from four to sixteen, and $R_1$, $R_2$, etc. are methyl, ethyl, n-propyl, n-butyl, and so on up to n-dodecyl. However a certain amount of branching within the alkyl and alkylene moieties may be tolerable if it does not adversely affect desired lubricant characteristics. Likewise the presence of aryl substituents (phenyl and the like) would generally be less desirable in the trisilahydrocarbons of our invention but might be tolerated if the product properties are not seriously compromised thereby. $R_1$, $R_2$, etc. may be the same or different alkyl groups, and —A— is considered to include mixtures of alkylene groups having different chain lengths within the four- to sixteen- carbon range. As will be shown hereinbelow, one of the outstanding characteristics of the trisilahydrocarbons of our invention is the ease with which, by suitable choice of chemical raw materials, a wide variety of different embodiments can be prepared thereof.

The trisilahydrocarbon lubricant base stocks of our invention are prepared by the following steps:

(a) Condensation of a diolefin having from four to sixteen carbon atoms or mixtures thereof with dihalosilanes, $X_2SiH_2$, wherein X is halogen and preferably chlorine or bromine, thereby forming the intermediate bis(alkenyl)dihalosilane:

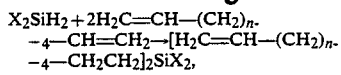

wherein n is from four to sixteen as above. This addition is carried out in the presence of a catalyst, such as hexachloroplatinic acid. A considerable excess of diolefin is employed in order to insure that only one of the two double bonds is reacted. The unreacted diolefin is subsequently recovered by distillation for further use.

(b) Condensation of the bis(alkenyl)dihalosilane from Step (a) with a trihalosilane or alternatively a trialkylsilane to form the bis(trihalosilylalkyl)dihalosilane or the bis(trialkylsilylalkyl)dihalosilane respectively:

wherein Y represents halogen, preferably chlorine or bromine, if a trihalosilane is used, or alternatively an alkyl group or mixed alkyl groups having from one to twelve carbon atoms if a trialkylsilane was used. Addition of the trihalo- and trialkylsilanes to double bond compounds are carried out in the presence of catalysts, as in the condensation reaction of Step (a) hereinabove.

It should be noted that, although addition reactions of dihalo-, trihalo-, and trialkylsilanes to olefinic compounds are old in the art, the specific intermediates prepared in Steps (a) and (b) are believed to be new compounds heretofor unknown. Moreover these intermediates are of an exceptional degree of utility in view of the vast numbers of synthetic lubricant products that can be prepared therefrom.

(c) Replacement of the halogen atoms in the intermediates of Step (b) with alkyl groups by treatment with organometallic compounds of suitable reactivity. The alkyl groups will contain from one to twelve carbon atoms. Suitable organometallic compounds include the alkyllithium compounds, alkylmagnesium halides (Grignard reagents), alkylsodium compounds, dialkylzinc compounds, and the like, with the alkyllithium compounds and the Grignard reagents being especially preferred. Mixtures of organometallic compounds can be employed (for example methyllithium plus n-butyllithium) to achieve mixed alkyl substitution in the final trisilahydrocarbon products.

As an alternative to the use of organometallic compounds, the halogen atoms can be replaced by hydrogen by treatment with hydridometallic reducing agents such as lithium aluminum hydride. The resulting —Si—H compounds can then be added to olefins in the presence of a suitable catalyst such as platinum acetylacetonate to form the final alkylsilicon products. The use of the organometallic compounds is considered preferable in order to avoid the two-step reaction sequence required by the alternative route. In either case, however, Step (c) results in the formation of a trisilahydrocarbon of our invention having the general formula $R_1R_2$—Si[—A—Si($R_3R_4R_5$)]$_2$.

As would be obvious to the skilled worker, numerous modifications in the structure of the final trisilahydrocarbon product can be achieved by the appropriate choice of the reactants used in each of the three steps. Higher molecular weight trisilahydrocarbons may be prepared by the use of a longer chain diolefin in Step (a), by the use of higher alkyl groups in the trialkylsilanes of Step (b), and by the use of higher alkyllithium compounds, alkylmagnesium halides, and the like in Step (c). Conversely the use of shorter chain diolefins and lower molecular weight alkyl compounds in (b) and (c) yield final trisilahydrocarbons with lower molecular weights. Reactants needed for the syntheses are in general readily available. The intermediates of Steps (a) and (b) can be prepared in bulk and used to prepare a wide range of trisilahydrocarbons by a suitable choice of organometallic compounds in Step (c). Thus the trisilahydrocarbons of our invention, as a class of synthetic lubricant, have the advantage of versatility, and can be "tailored" to achieve a wide range of lubricant properties.

The preparation of trisilahydrocarbons of our invention will now be illustrated by specific Examples.

EXAMPLE 1

Preparation of Bis(8-trimethylsilyloctyl)dimethylsilane ($R_{1-5}$=methyls, —A—=—$C_8H_{16}$—)

Step (a)

To a 100 ml glass ampoule equipped with a magnetic stirring bar was added hexachloroplatinic acid (0.15 ml, 0.090M solution in isopropanol). After the solvent was removed under reduced pressure, 1,7-octadiene (14.39 g, 130.6 mmoles) and dichlorosilane (2.08 g, 20.82 mmoles) were condensed in vacuo into the ampoule. The ampoule was sealed off, placed in an oil bath, and heated gradually to the final reaction temperature of 60° C. at which it was kept for 120 hours. After opening the ampoule into a vacuum line and observing no condensibles, the excess 1,7-octadiene was distilled off to yield 6.02 g (90.0% yield) of bis(octenyl)dichlorosilane. Step (b)

To a 100 ml glass ampoule equipped with a magnetic stirring bar was added hexachoroplatinic acid (0.05 ml, 0.090M solution in isopropanol). After the solvent was removed under reduced pressure, bis(octenyl)dichlorosilane (6.02 g, 18.74 mmoles) was introduced into the ampoule in an inert atmosphere enclosure. Subsequently trichlorosilane (29.9 g, 198.6 mmoles) was condensed into the ampoule on the vacuum line. The in vacuo sealed ampoule was placed in an oil bath and heated up slowly to 110° C. at which temperature it was kept for twenty four hours. After opening the ampoule into the vacuum line, a small quantity of noncondensibles was observed. The excess trichlorosilane was distilled off to yield 10.53 g (94.9% yield) of bis (8-trichlorosilyloctyl)dichlorosilane.

Step (c)

In an inert atmosphere, bis(8-trichlorosilyloctyl)dichlorosilane (5.00 g, 8.45 mmoles) was charged to a 100 ml roundbottom flask equipped with a Claisen adaptor, reflux condenser, addition funnel, septum for hypodermic additions, magnetic stirring bar, and nitrogen bypass inlet. Methyllithium (58 ml of a 1.4M solution in diethyl ether) was introduced via syringe over a period of 15 minutes under nitrogen atmosphere, with cooling from an ice water bath around the outside of the flask. A powdery white precipitate appeared immediately. The mixture was allowed to stir at room temperature for 16 hours and then gently refluxed for 7 hours. It was then cooled in an ice water bath and cautiously added to a vigorously stirred cool solution of hydrochloric acid (150 ml, 1.2N). After addition of 100 ml of diethyl ether, the organic layer was separated, water-washed, and dried over anhydrous magnesium sulfate. Removal of the solvent gave 3.41 g (94.5% yield) of the trisilahydrocarbon product, bis(8-trimethylsilyloctyl)dimethyl silane. The trisilahydrocarbon had a kinematic viscosity of 3.93 centistokes at 100° C., a kinematic viscosity of 15.2 centistokes at 40° C., and a viscosity index of 164. Onset of volatility, based on thermogravimetric analysis, was at about 135° C. The viscosity index indicates viscosity-temperature characteristics superior to those of the synthetic hydrocarbon (polyalphaolefin) used as the base stock in aircraft hydraulic fluids meeting Military Specification MIL-H-83282 (the viscosity index of which is normally around 130).

EXAMPLE 2

Preparation of a Higher Molecular Weight Trisilahydrocarbon ($R_{1-5}$ predominately n-octyl, —A—=—$C_8H_{16}$—)

In this experiment, the bis(8-trichlorosilyloctyl)dichlorosilane prepared in Example 1, Step (b), was reacted, first with an excess of n-octylmagnesium bromide in tetrahydrofuran, then with methyllithium in ether to insure removal of all chlorine from the final product. A 48% yield of a trisilahydrocarbon was obtained. It had a kinematic viscosity of 109.4 centistokes at 40° C. The onset of volatility, based on thermogravimetric analysis, was at about 280° C. Thus it was shown that by use of a higher-alkyl organometallic compound in Step (c), a far more viscous trisilahydrocarbon product with much lower volatility could be prepared from the same intermediate as was used to prepare the relatively low viscosity base stock of Example 1.

As would be obvious to one skilled in the art, numerous modifications can be made herein without departing from the scope of our invention. The trisilahydrocarbon synthetic lubricant base stocks can be used as prepared; or alternately, they can be formulated with additives designed to impart additional desirable properties appropriate to the application—for example, antioxidants, corrosion inhibitors, antiwear agents, detergents, antifoam agents, and the like. The above Examples are for purposes of illustration only, and are not meant to be limiting within the scope of the following claims.

We claim:

1. A trisilahydrocarbon synthetic lubricant base stock having the general formula $$R_1R_2—Si[—A—Si(R_3R_4R_5)]_2$$

wherein $R_1$, $R_2$, $R_3$, $R_4$, and $R_5$ are alkyl groups having from one to twelve carbon atoms and mixtures thereof and —A— is an alkylene group or mixture of alkylene groups having from four to sixteen carbons.

2. The trisilahydrocarbon synthetic lubricant base stock of claim 1 wherein the alkyl and alkylene groups are unbranched.

3. The trisilahydrocarbon synthetic lubricant base stock of claim 1 wherein the alkyl groups are methyl and the alkylene group is octamethylene.

4. A trisilahydrocarbon synthetic lubricant base stock prepared by the following steps:
   (a) condensation of a diolefin having from four to sixteen carbon atoms or mixtures of said diolefins with dihalosilane to form a bis(alkenyl)dihalosilane;
   (b) condensation of the bis(alkenyl)dihalosilane of Step (a) with a trihalosilane or trialkylsilane wherein the alkyl groups contain from one to twelve carbon atoms to form a bis(trihalosilylalkyl)dihalosilane or bis(trialkylsilylalkyl)dihalosilane respectively;
   (c) substitution of the halogen atoms in the products of Step (b) with alkyl groups having from one to twelve carbon atoms by treatment with organometallic compounds selected from allkyllithium compounds, alkylmagnesium halides, alkylsodium compounds, and dialkylzinc compounds or alternatively by treatment with hydridometallic reducing agents with lithium aluminum hydride being preferred to from Si—H compounds which are then added to olefins in the presence of a suitable catalyst such as platinum acteylacetonate to form the final alkylsilicon products.

5. As chemical intermediates, bis(alkenyl)dihalosilanes wherein the alkenyl group contains from four to sixteen carbon atoms, bis(trihalosilylalkyl) dihalosilanes wherein the silylalkyl moiety contains from four to sixteen carbon atoms, and bis(trialkylsilylalkyl)dihalosilanes wherein the alkyl groups contain from one to twelve carbon atoms and the silylalkyl moiety contains from four to sixteen carbon atoms.

* * * * *